(12) United States Patent
Kaiser

(10) Patent No.: US 8,399,399 B2
(45) Date of Patent: Mar. 19, 2013

(54) 3- AND 4-METHYL DODECENAL AND THEIR USE IN FRAGRANCE AND FLAVOUR COMPOSITIONS

(75) Inventor: Roman Kaiser, Uster (CH)

(73) Assignee: Givaudan SA, Vernier (CH)

( * ) Notice: Subject to any disclaimer, the term of this patent is extended or adjusted under 35 U.S.C. 154(b) by 780 days.

(21) Appl. No.: 11/917,201

(22) PCT Filed: Jun. 15, 2006

(86) PCT No.: PCT/CH2006/000321
§ 371 (c)(1),
(2), (4) Date: Dec. 12, 2007

(87) PCT Pub. No.: WO2006/133591
PCT Pub. Date: Dec. 21, 2006

(65) Prior Publication Data
US 2008/0248177 A1    Oct. 9, 2008

(30) Foreign Application Priority Data

Jun. 17, 2005 (EP) .................................... 05013109

(51) Int. Cl.
| | | |
|---|---|---|
| A61K 8/18 | (2006.01) | |
| A61K 8/00 | (2006.01) | |
| A61K 9/68 | (2006.01) | |
| A61K 8/02 | (2006.01) | |
| A61Q 13/00 | (2006.01) | |
| C07C 47/00 | (2006.01) | |
| C11D 3/50 | (2006.01) | |
| C11D 3/02 | (2006.01) | |
| C11D 9/44 | (2006.01) | |

(52) U.S. Cl. .............. 512/27; 512/1; 568/420; 510/105; 510/108; 424/48; 424/401; 424/70.1

(58) Field of Classification Search .................... 512/27, 512/1; 568/420; 510/105, 108; 424/48, 424/401, 70.1
See application file for complete search history.

(56) References Cited

U.S. PATENT DOCUMENTS 3,920,752 A * 11/1975 Lamparsky .................. 568/448
3,928,402 A    12/1975 Naf et al.

* cited by examiner

*Primary Examiner* — Patrick Ryan
*Assistant Examiner* — Aaron Greso
(74) *Attorney, Agent, or Firm* — Norris McLaughlin & Marcus PA

(57) ABSTRACT

3- and 4-Methyl-4-dodecenal, a method of their production and fragrance and flavor compositions comprising at least one of them.

5 Claims, No Drawings

3- AND 4-METHYL DODECENAL AND THEIR USE IN FRAGRANCE AND FLAVOUR COMPOSITIONS

This is an application filed under 35 USC 371 of PCT/CH2006/000321.

The present invention refers to 3- and 4-methyl-4-dodecenal, to a method of their production and to fragrance and flavour compositions comprising at least one of them.

In the fragrance industry there is a constant demand for new compounds that enhance or improve on odour notes. Of particular interest are those that impart powerful odour notes to the characteristic of a fragrance composition, even if used in very small concentration.

γ,δ-unsaturated aldehydes and their use as odorants and flavorants are well known in the art and disclosed for example in GB 1,305,281. However, the compounds of the present invention have never been described in literature, and are novel.

Surprisingly, it has been found that the compounds of the present invention, when compared with their structural isomer 2-methyl-4-dodecanal, are characterized by an odour threshold concentration which is up to 64 times lower. The odour threshold concentration is defined as the lowest concentration of the vapour of an odourant material in the air which can be detected by smell and can be measured by standard methods known in the art.

Because of their very low odour threshold concentration, it is possible to use much lower concentrations of the compounds of the present invention compared to 2-methyl-4-dodecenal to achieve an olfactory effect, which makes them particularly useful and appreciated for the preparation of perfume, perfuming compositions and perfumed products.

Thus the present invention refers in one of its aspects to the use as fragrance or flavour of a compound of formula

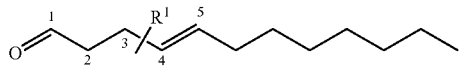

wherein $R^1$ represents a methyl group in C-3 or C-4 position; and the double bond between C-4 and C-5 is in E or Z configuration.

Whereas the (Z)- and (E)-isomers show similar olfactory profiles, the odour threshold of the (Z)-isomer compared to its corresponding (E)-isomer is higher, i.e. that of pure (Z)-3-methyl-4-dodecenal is 5 times higher than that of the pure (E)-3-methyl-4-dodecenal and that of pure (Z)-4-methyl-4-dodecenal is 20 times higher than that of the pure (E)-4-methyl-4-dodecenal. Accordingly, the use of the pure (E)-isomer is preferred. However, a mixture of both isomers, preferably enriched in the (E)-isomer, which is readily available synthetically, can also be used.

The term "enriched" is used herein to describe the compounds of the present invention having an isomeric purity greater than 1:1 in favour of the (E)-isomer. Particularly preferred are compounds having an isomeric purity of 3:1 (E:Z), more preferably 4:1 (E:Z), and most preferably 5:1 (E:Z) or greater.

The compounds of the present invention may be used in a broad range of fragrance applications, e.g. in any field of fine and functional perfumery, such as perfumes, household products, laundry products, body care products, cosmetics and air-care products. The compounds can be employed in widely varying amounts, depending upon the specific application and on the nature and quantity of other odorant ingredients. Quite generally it can be said that the compounds as hereinabove described are very powerful odorants and, therefore, effects may already be obtained at very low dosage, e.g. 0.005 weight percent. On the other side they can be used even at very high concentrations, if combined with the optimal partners. The preferred concentration varies between about 0.005 weight percent and about 20 weight percent, preferably between 0.01 and 5 weight percent based on the end product. However, these values are given only by way of example, since the experienced perfumer may also achieve effects or may create novel accords with lower or higher concentrations.

In one embodiment, 4-methyl-4-dodecenal may be employed in a fabric softener in an amount of from 0.005 to 0.2 weight percent. In another embodiment, 4-methyl-4-dodecenal may be used in fine perfumery in amounts of from 0.01 to 5 weight percent, more preferably between 0.01 and 0.5 weight percent.

The compounds of the present invention can be used for the creation of a very broad spectrum of fragrance and flavour compositions by admixing it with a base material. As used herein, the "base material" includes all known odourant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odourants in fragrance compositions, for example, carrier materials, and other auxiliary agents commonly used in the art.

The following list comprises examples of known odourant molecules, which may be combined with the compounds of the present invention:

essential oils and extracts, e.g. tree moss absolute, basil oil, castoreum, costus root oil, myrtle oil, oak moss absolute, geranium oil, jasmin absolute, patchouli oil, rose oil, sandalwood oil, wormwood oil, lavender oil or ylang-ylang oil;

alkohols, e.g. citronellol, Ebanol™, eugenol, farnesol, geraniol, Super Muguet™, linalool, phenylethyl alcohol, Sandalore™, terpineol or Timberol™;

aldehydes and ketones, e.g. α-amylcinnamaldehyde, Georgywood™, hydroxycitronellal, Iso E Super®, Isoraldeine®, Hedione®, maltol, methyl cedryl ketone, methylionone or vanillin;

ethers and acetals, e.g. Ambrox™, geranyl methyl ether, rose oxide or Spirambrene™;

esters and lactones, e.g. benzyl acetate, cedryl acetate, γ-decalactone, Helvetolide®, γ-undecalactone or Vetivenyl acetate;

macrocycles, e.g. ambrettolide, ethylene brassylate or Exaltolide®;

heterocycles, e.g. isobutylchinoline.

The compounds of the present invention may be employed into the fragrance application simply by directly mixing the fragrance composition with the fragrance application, or it may, in an earlier step be entrapped with an entrapment material, for example, polymers, capsules, microcapsules and nanocapsules, liposomes, film formers, absorbents such as carbon or zeolites, cyclic oligosaccharides and mixtures thereof, or it may be chemically bonded to substrates, which are adapted to release 3-methyl-4-dodecenal and 4-methyl-4-dodecenal respectively upon application of an external stimulus such as light, enzyme, or the like, and then mixed with the application.

Thus, the invention additionally provides a method of manufacturing a fragrance application, comprising the incorporation of a compound according to the present invention as a fragrance ingredient, either by directly admixing it to the application or by admixing a fragrance composition comprising at least one compound as herein above described, which may then be mixed to a fragrance application, using conventional techniques and methods.

As used herein, "fragrance application" means any product, such as fine fragrance, e.g. perfume and eau de toilette; household products, e.g. detergents for dishwasher, surface cleaner; laundry products, e.g. softener, bleach, detergent; body care products, e.g. shampoo, shower gel; and cosmetics, e.g. deodorant, vanishing creme, comprising an odourant. This list of products is given by way of illustration and is not to be regarded as being in any way limiting.

The compounds of the present invention may be prepared for example by a Claisen type rearrangement under conditions well known in the art.

The invention is now further described with reference to the following non-limiting examples.

EXAMPLE 1

Synthesis of (E/Z)-4-methyl-4-dodecenal a) 2-Methyl-1-decen-3-ol

Under an atmosphere of nitrogen the reaction flask is charged with 9.85 g magnesium and 100 ml diethyl ether. The Grignard reaction is started with 3.00 g bromo-heptane. Then a solution of 70.00 g bromo-heptane in 50 ml diethyl ether is added dropwise within 90 minutes, the reaction mixture is kept at mild reflux and subsequently cooled to 0° C. to add now within 30 minutes a solution of 28.70 g 2-methyl-2-propenal in 30 ml diethyl ether. After further stirring for 2 hours at room temperature the reaction mixture is again cooled to 0° C. and 50 ml of diluted hydrochloric acid (3.5%) are carefully added. The organic layer is washed with water, dried with sodium sulfate and subsequently concentrated to give 86.7 g crude material. Distillation over a 10 cm-column (Widmer type) gives 40.5 g 2-methyl-1-decen-3-ol having a boiling point of 75° C. at 0.12 bar.

b) 4-Methyl-4-dodecenal

Under an atmosphere of nitrogen, the autoclave (300 ml) is charged with 43.0 g 2-methyl-1-decen-3-ol (0.25 mol), 60.0 g (0.60 mol) butyl vinyl ether and 0.10 g catalyst (10.0 g phosphoric acid (85%) and 10 g triethanolamine are mixed (exothermic reaction) giving rise to a whitish semi-solid, 0.10 g being used in this experiment). The autoclave is closed and purged three times with nitrogen under stirring and then pressurized with nitrogen to 3 bar. The reaction mixture is now heated to 220° C. and the pressure rises within the first hour to 10 bar to fall then to 8 bar. After 3 hours of total reaction time the mixture is allowed to cool, removed from the autoclave, filtered, washed with a 5%-solution of sodium bicarbonate in water, dried and concentrated at 50° C./50 mbar (rotary evaporator) to 56.0 g of crude product. Distillation of this material over a 10 cm-column (Widmer type) gives 25.0 g (E,Z)-4-methyl-4-dodecenal (4:1) with a boiling point of 62° C. at 0.12 bar.

The (E)-isomer was characterized by measuring the 4:1 mixtures, the (Z)-isomer was isolated by preparative capillary gas chromatography and subsequently characterized by measuring the spectral data.

(E)-4-Methyl-4-dodecenal:
$^1$H-NMR (400 MHz, CDCl$_3$): 9.76 (t, J=1.8, 1H), 5.16 (tsx, J$_1$=7.3, J$_2$=1.3, 1H), 2.51 (m, 2H), 2.32 (t, J=7.6, 2H), 1.97 (q, J=6.6, 2H), 1.61 (s, 3H), 1.34-1.21 (m, 10H), 0.88 (t, J=7.1, 3H).
MS (El): 196 (1, M$^+$), 178(11), 152(21), 109(13), 95(35), 93(30), 83(46), 81(47), 68(52), 55(100), 43(42), 41(77).

(Z)-4-Methyl-4-dodecenal:
$^1$H-NMR (500 MHz, C$_6$D$_6$): 9.32 (t, J=1.6, 1H), 5.15 (t, J=7.3, 1H), 2.13 (t, J=7.6, 2H), 1.96-1.89 (m, 4H), 1.50 (s, 3H), 1.33-1.20 (m, 10H), 0.90 (t, J=7.3, 3H).
MS (El): 196 (1, M$^+$), 178(12), 152(22), 109(15), 95 (41), 93 (30), 83 (45), 81 (53), 68 (61), 55(100), 43 (41), 41(80).

Odor description: aldehydic, orange, mandarin, slightly woody for (E)-4-methyl-4-dodecenal. (Z)-4-Methyl-4-dodecenal is similar to the (E)-isomer, but the aldehydic, waxy aspects are somewhat more pronounced.

EXAMPLE 2

Syntheses of (E/Z)-3-methyl-4-dodecenal a) Undec-2-en-4-ol

Under an atmosphere of nitrogen the flask is charged with 121 g magnesium and 720 g tetrahydrofuran. The Grignard-reaction is started with 5 g bromo-heptane. Then, a solution of 908 g bromo-heptane in 1000 g toluene is added dropwise within 260 minutes under stirring. The reaction mixture is kept between 55 and 60° C. The resulting dark solution is cooled to 10° C. and a solution of 357 g crotonaldehyde in 500 g toluene is added dropwise within 105 minutes, during which the pot temperature is kept between 10 and 20° C. with an ice-water bath. The resulting grey-brown suspension is continued to stir for 20 minutes at max. 20° C. and then poured, under vigorous stirring, into a mixture of 2 kg ice and 1 l aqueous saturated ammonium chloride solution. The mixture is diluted with 4 l water and buffered with 300 ml acetic acid. The phases are separated. The organic layer is washed with 4 l and 2 l hot water. The organic phase is concentrated in vacuo to give 864 g crude product as a pale yellow oil. This is distilled at 0.1 mbar over a 10 cm-Raschig ring column. Fractions boiling between 85 and 90° C. were collected to give 709 g undec-2-en-4-ol.

b) 3-Methyl-4-dodecenal

Under an atmosphere of nitrogen, the autoclave is charged with 170 g undec-2-en-4-ol, 173 g ethyl vinyl ether and 1.3 g triethanolammonuim dihydrogenphosphate. The autoclave is closed and purged three times with nitrogen under stirring and then pressurised with nitrogen to 2 bar. Heating is applied and the mixture is stirred at 170° C. for 45 minutes before the temperature is raised to 200° C. for further 75 minutes.

The mixture is allowed to cool, removed from the autoclave, filtered and concentrated in vacuo to give 213 g crude product as a pale brown oil. This material is distilled at 0.5 mbar over a 25 cm-column, packed with steel spirals (3×4 mm). Fractions boiling at 84-86° C. are judged olfactorily pure and give a total of 79 g 3-methyl-dodec-4-enal as a colourless liquid.

Separation of (E)- and (Z)-isomers was performed by preparative capillary gas chromatography.

(E)-3-Methyl-4-decenal:
$^1$H-NMR (400 MHz, CDCl$_3$): 9.72 (t, J=2.5, 1H), 5.44 (dtd, J$_1$=15.4, J$_2$=6.6, J$_3$=0.8, 1H), 5.34 (ddt, J$_1$=15.4, J$_2$=6.8, J$_3$=1.1, 1H), 2.72 (m, J=6.8, 1H), 2.41 (ddd, J$_1$=16.2, J$_2$=7.3, J$_3$=2.5, 1H), 2.33 (ddd, J$_1$=16.2, J$_2$=6.8, J$_3$=2.5, 1H), 1.97 (q, J=7.1, 2H), 1.39-1.20 (m, 10H ), 1.06 (d, J=6.8, 3H ), 0.88 (t, J=6.9, 3H ).

MS (EI): 196 (1, M+), 181 (7), 152 (11), 111 (28), 98 (78), 97 (100), 83 (23), 69 (49), 55 (84), 41 (81).

(Z)-3-Methyl-4-decenal:

$^1$HNMR (400 MHz, CDCl$_3$): 9.34 (t, J=2.2, 1H), 5.29 (dtd, J$_1$=11.0, J$_2$=7.3, J$_3$=0.9, 1H), 5.02 (ddt, J$_1$=11.0, J$_2$=9.8, J$_3$=1.6, 1H), 2.83 (dqtd, J$_1$=9.8, J$_2$=6.6, J$_4$=0.95, 1H), 1.97 (m, 1H), 1.89 (ddd, J$_1$=16.1, J$_2$=7.6, J$_3$=2.2, 1H), 1.83 (ddd, J$_1$=16.1, J$_2$=6.6, J$_3$=2.2, 1H), 1.36-1.19 (m, 10H), 0.90 (d, J=6.9, 3H), 0.80 (d, J=6.6, 3H).

MS (EI): 196 (1, M+), 181 (5), 152 (8), 111 (22), 98 (72), 97 (82), 83 (25), 81 (29), 69 (52), 55 (89), 43 (59), 41 (100).

Odor description: aldehydic, citrus-related, slightly carrot for (E)-3-methyl-4-dodecenal. (Z)-3-methyl-4-dodecenal is similar to the (E)-isomer, but the aldehydic, waxy aspects are somewhat more pronounced.

EXAMPLE 3

Determination of GC-odour threshold concentration

According to standard procedures known to the person skilled in the art, threshold concentrations for volatile perfumery compounds are determined on a gas chromatograph equipped with a sniff port by a panel of trained evaluators. The lowest concentration smelled by each panellist is recorded as the individual threshold concentration expressed in ng (absolute amount of compound delivered at the sniff port).

Under identical conditions the odour threshold concentration for (E)-2-methyl-4-dodecenal (prior art), (E)-3-methyl-4-dodecenal and (E)-4-methyl-4-dodecenal was measured and compared by a group of 5 panelists. The results are given below.

| Compound | odour threshold concentration [ng] geometric mean |
|---|---|
| (E)-2-methyl-4-dodecenal | 3.2 |
| (E)-3-methyl-4-dodecenal | 1.0 |
| (E)-4-methyl-4-dodecenal | 0.05 |

It can be seen from the results that the compounds of the present invention have an odour threshold value with is up to 64 times lower compared to (E)-2-methyl-4-dodecenal. Based on this, a significant advance is achieved because much smaller amounts of the claimed compounds is required to impart the same odour.

In particular (E)-4-methyl-4-dodecenal is characterized by its remarkable low odour threshold concentration of 0.05 ng. To the best of our knowledge no other aldehyde of this structural class shows a comparably low threshold value.

EXAMPLE 4

Fragrance composition of rosy-floral character

| Compounds | Parts by weight 1/1000 |
|---|---|
| Lemon oil Italy | 20 |
| Mandarin oil/green Italy | 10 |
| cis-3-Hexenyl acetate 10% in DPG | 7 |
| Hexyl acetate 10% in DPG | 5 |
| Cis-3-Hexenol 10% in DPG | 3 |
| Rose oxide 10% in DPG | 2 |
| Farnesene | 30 |
| Linalol synth. | 10 |
| Phenylacetaldehyde 10% in DPG | 10 |
| Menthone | 5 |
| Menthol | 2 |
| Citral | 10 |
| Citronellyl acetate | 8 |
| Neryl acetate | 20 |
| Geranyl acetate | 25 |
| Phenylethyl acetate | 20 |
| Rhodinol pur | 50 |
| Nerol | 50 |
| Geraniol | 150 |
| Phenylethyl alcohol | 150 |
| Dihydro-beta-ionone | 20 |
| Beta-Ionone | 40 |
| beta-Damascone 10% in DPG | 1 |
| Eugenol | 4 |
| Gamma-Decalactone 10% in DPG | 5 |
| Adoxal | 3 |
| Nerolidaol | 20 |
| Farnesol | 20 |
| Benzyl benzoate | 30 |
| Indole | 1 |
| 2(3)-Dihydrofarnesal | 30 |
| Dipropylenglycol | 239 |
| Total | 10000 |

This fragrance accord is characterized by a refreshing rosy-floral note reminiscent of certain Tea roses. Addition of 8 parts of a 1%-solution of (E/Z)-4-methyl-4-dodecenal (about 4:1) supports especially the top note by conferring to it a very interesting marine and citrus-related aspect.

EXAMPLE 5

Fragrance of fresh hesperidic, woody character

| Compound | Parts by weight 1/1000 |
|---|---|
| Lemon oil Italy | 15 |
| Bergamot oil Italy | 15 |
| Eucalyptol | 4 |
| Rose oxide at 1% in DPG | 8 |
| Ginger extract CO$_2$ | 30 |
| Bornyl acetate | 15 |
| Linalol synt. | 15 |
| Linalyl acetate synt. | 30 |
| Caryophyllene | 15 |
| Farnesene isomers | 15 |
| alpha-Terpineol | 15 |
| Citral | 2 |
| Geranyl acetate | 25 |
| Citronellol | 10 |
| Geraniol | 15 |
| Adoxal | 2 |
| Georgywood | 70 |
| Vetynal extra | 70 |
| Dihydrofarnesal | 35 |
| Nerolidol extra | 40 |
| Farnesol synt. | 60 |
| Thibetolide | 75 |
| Ambrettolide | 50 |
| Ethylene brassylate | 20 |
| Cedryl acetate | 30 |
| Nutmeg oil Indonesia | 5 |
| Dipropylene glycol | 314 |

The above fragrance is of refreshing citrus-related character, completed by woody, rosy-floral and musky note. Addition of 15 parts of a 1%-solution of (E/Z)-4-methyl-4-dodecenal makes the fragrance even more refreshing and radiant, adds an attractive marine note and enhances an appealing aspect reminiscent of fresh ginger roots.

EXAMPLE 6

Fragrance composition of fresh floral character

| Compound | Parts by weight 1/1000 |
|---|---|
| Lemon oil Italy | 20 |
| Bergamot oil Italy | 40 |
| cis-3-Hexenyl acetate | 3 |
| cis-3-Hexenol | 2 |
| Linalol synt. | 70 |
| Linalyl acetate synt. | 30 |
| Gardenol | 20 |
| Rhodinol pur | 40 |
| Phenylethyl alcohol | 35 |
| Dihydro-beta-ionone | 20 |
| Beta-Ionone | 30 |
| 2,3-Dihydrofarnesal | 60 |
| Nerolidol (3,7,11-Trimethyl-1,6,10-dodecatrien-3-ol) | 50 |
| Lilial | 30 |
| cis-3-Hexenyl benzoate | 30 |
| cis-3-Hexenyl salicylate | 20 |
| Hedione (methyl dihydrojasmonate) | 100 |
| Sandalore (5-(2,2,3-trimethylcyclopent-3-en-1-yl)-3-methylpentan-2-ol) | 35 |
| Iso E super (octahydro-2,3,8,8-tetramethyl-2-acetonaphthone) | 50 |
| Thibetolide (omega-pentadecalactone) | 25 |
| Nirvanolide (12-methyl-9-tetradecen-14-olide) | 35 |
| Benzyl benzoate | 55 |
| Benzyl salicylate | 30 |
| Dipropylene glycol (DPG) | 170 |
| Total | 1000 |

The above fragrance of fresh floral character consists of white-floral, rosy-floral, ionone-floral musky and woody notes, completed by a citrus-related top note.

Addition of 10 parts of (E/Z)-3-methyl-4-dodecenal (about 15:1) supports especially the top note by conferring to it a very interesting marine note and a note related to citrus fruits. These effects could not be achieved by using existing fragrance products.

EXAMPLE 7

Fragrance composition of fresh hesperidic, woody character

| Compound | Parts by weight 1/1000 |
|---|---|
| Lemon oil Italy | 15 |
| Bergamot oil Italy | 15 |
| Eucalyptol | 4 |
| Rose oxide at 1% in DPG | 8 |
| Ginger extract $CO_2$ | 30 |
| Bornyl acetate | 15 |
| Linalol synt. | 15 |
| Linalyl acetate synt. | 30 |
| Caryophyllene | 15 |
| Farnesene isomers | 15 |
| alpha-Terpineol | 15 |
| Citral | 2 |

-continued

| Compound | Parts by weight 1/1000 |
|---|---|
| Geranyl acetate | 25 |
| Citronellol | 10 |
| Geraniol | 15 |
| Adoxal (2,6,10-trimethyl-9-undecenal) | 2 |
| Georgywood* | 70 |
| Vetynal extra (caryophyllene acetate) | 70 |
| 2,3-Dihydrofarnesal | 35 |
| Nerolidol extra | 40 |
| Farnesol synt. | 60 |
| Thibetolide | 75 |
| Ambrettolide | 50 |
| Ethylene brassylate | 20 |
| Cedryl acetate | 30 |
| Nutmeg oil Indonesia | 5 |
| Dipropylene glycol (DPG) | 314 |
| Total | 1000 |

*1-(1,2,8,8-Tetramethyl-1,2,3,4,5,6,7,8-octahydro-naphthalen-2-yl)-ethanone

The above fragrance is of very refreshing hesperidic (citrus-related) character, completed by woody, rosy-floral and musky notes. Addition of 15 parts by weight of (E/Z)-3-methyl-4-dodecenal (about 15:1) makes the fragrance more diffusive and radiant and strongly enhances an appealing aspect reminiscent of fresh ginger roots. These effects could not be achieved in these qualities by using existing fragrance products.

EXAMPLE 8

Fragrance/Flavor base of citrus-related character

| Compound | Parts by weight 1/1000 |
|---|---|
| Lemon oil Italy | 300 |
| Grapefruit oil | 100 |
| cis-3-Hexenol 10% in DPG | 5 |
| cis-3-Hexenyl acetate 10% in DPG | 4 |
| trans-2-Dodecenal 10% in DPG | 2 |
| Linalol synt. | 10 |
| Beta-Ionone | 3 |
| Nerol extra | 10 |
| Nerolidol extra | 50 |
| Farnesol synt. | 50 |
| 2,3-Dihydrofarnesal | 50 |
| Cedrol crist. extra | 10 |
| cis-3-Hexenyl benzoate | 2 |
| Methyl jasmonate | 30 |
| Citral | 20 |
| Dipropylene glycol (DPG) | 354 |
| Total | 1000 |

The above fragrance/flavor accord is of citrus related character and can be used in the fragrances as well as in the flavor field. Addition of 10 parts of (E/Z)-3-methyl-4-dodecenal (about 15:1) enhances the diffusion and radiance of this accord and confers to it a very interesting zesty note. These effects could not be achieved in these qualities by using existing fragrance products.

The invention claimed is:

1. A compound of the formula

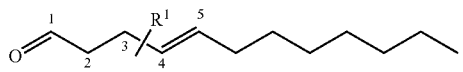

wherein:
$R^1$ represents a methyl group in the C-4 position; and
the double bond between C-4 and C-5 is in an E configuration,
characterized in that when $R^1$ is a methyl group in the C-4 position, the compound has an odor threshold value about 64 times lower than (E)-2-methyl-4-dodecenal.

2. A fragrance or flavour composition comprising a compound according to claim 1.

3. A fragrance application comprising a compound of claim 1.

4. A fragrance application of claim 3 wherein the fragrance application is selected from the group consisting of: perfume material, household product, laundry product, body care product, cosmetic product and air-care product.

5. A method of manufacturing a fragrance or flavor application comprising the step of incorporating a compound of claim 1 into the fragrance or flavor application.

* * * * *